United States Patent [19]
Gottlieb et al.

[11] Patent Number: 5,244,929
[45] Date of Patent: Sep. 14, 1993

[54] MOLDED BODIES COMPRISED OF MACROPOROUS ION EXCHANGE RESINS, AND USE OF SAID BODIES

[75] Inventors: Klaus Gottlieb, Herdecke; Wilfried Graf, Dorsten; Kuno Schädlich, Essen; Ulrich Hoffmann, Braunschweig; Alwin Rehfinger, Mutterstadt; Jörg Flato, Osterrode, all of Fed. Rep. of Germany

[73] Assignee: Veba Oel Aktiengesellschaft, Gelsenkirchen, Fed. Rep. of Germany

[21] Appl. No.: 882,770

[22] Filed: May 11, 1992

Related U.S. Application Data

[63] Continuation of Ser. No. 581,529, Sep. 12, 1990.

[30] Foreign Application Priority Data

Sep. 13, 1989 [DE] Fed. Rep. of Germany ....... 3930515

[51] Int. Cl.$^5$ .............................. C08F 5/20; C08F 5/22
[52] U.S. Cl. .......................................... 521/29; 521/25; 521/31; 521/32; 521/33; 521/38; 525/343; 525/370; 525/371; 526/336; 526/340; 526/347

[58] Field of Search ....................... 521/29, 31, 32, 33; 525/245, 370

[56] References Cited

U.S. PATENT DOCUMENTS

| | | | |
|---|---|---|---|
| 3,248,339 | 4/1966 | Spes et al. | 521/28 |
| 3,847,840 | 11/1974 | Kanig | 521/64 |
| 4,007,138 | 2/1977 | Kanig | 521/64 |
| 4,012,456 | 3/1977 | Chaplits | 568/899 |

FOREIGN PATENT DOCUMENTS 0104912 1/1988 European Pat. Off. .

OTHER PUBLICATIONS

J58133821–English Abstract.

*Primary Examiner*—Joseph L. Schofer
*Assistant Examiner*—Fred Zitomer
*Attorney, Agent, or Firm*—Oblon, Spivak, McClelland, Maier & Neustadt

[57] ABSTRACT

Molded bodies in the form of packing bodies comprising a macroporous strongly acid or basic ion exchange resin having a voids fraction of 5–95 vol % of the macro shape without pores, a BET surface area of 0.1–1,000 sq m/g, and an ion exchange capacity of 0.05–10 meq/g.

10 Claims, 4 Drawing Sheets

MOLDED BODIES COMPRISED OF MACROPOROUS ION EXCHANGE RESINS, AND USE OF SAID BODIES

This application is a continuation of application Ser. No. 07/581,529, filed on Sep. 12, 1990, now abandoned.

BACKGROUND OF THE INVENTION

1. Field of the Invention

The invention relates to molded bodies comprised of macroporous ion exchange resins, and to the use of such bodies

2. Description of the Background

Macroporous ion exchange resins are known as packings, e.g. for chromatography columns. Thus in Eur OS 01 04 912 A the separation of sugars by liquid chromatography over a column filled with porous sulfonated divinylbenzene-styrene copolymer is described. The packing is present in particle sizes of 1-30 micron.

In the 1988 dissertation of A. Rehfinger, at Technische Universitaet Clausthal, a reexamination of the catalytic etheration of isobutene and methanol to form methyl tert-butyl ether (MTBE) over a macroporous strongly acid ion exchange resin was carried out. The particle size of the catalyst used was in the range 0.3-1.2 mm.

In Jap. Pat. 58-133,821 A, in a method of exchanging hydrogen for deuterium in an equilibrium reaction between gaseous hydrogen and steam, the catalyst used comprised a platinized hydrophobic material, comprised of a styrene-divinylbenzene copolymer or the like, as a support, in the form of spheres, pellets, woven or knitted surface structures, Raschig rings, or the like. The catalyst is mounted in a reticular structure comprised of stainless steel or plastic resin material which prevents passage of liquid water.

In Arganbright, R. P., Hearn, Dennis, Jones, Edward M , and Smith, Lawrence (all of Chemical Research and Licensing Company and/or Neochem Corporation), September 1986, DOE/CS/40 454-T3, a final report document, a method of producing MTBE by catalytic distillation is described, which enables simultaneous catalysis and distillation in a reaction apparatus. As catalyst, a sulfonated divinylbenzene-styrene copolymer is used, in particle sizes of 0.1-0.5 mm, with the particles accommodated in pockets in belt-like strips of fiberglass fabric, which pockets are produced by sewing into the strips. After the pockets are filled, their openings are also closed by sewing, and with the aid of interposed layers of a stainless steel wire mesh structure with mesh size 12 in, the strip is rolled to form cylindrical bodies which are inserted into a fixed bed-reactor column.

This method has the disadvantage that the mass transport is substantially lessened because of the covering of the ion exchange material. A need therefore continues to exist for molded bodies of macroporous material of improved characteristics.

SUMMARY OF THE INVENTION

Accordingly, one object of the present invention is to provide means of promoting various types of chemical reactions along with separation of components of the reaction mixtures in the presence of a catalytically active packing which catalyzes the reaction and facilitates the intensive mass transfer needed for the separation.

Briefly, these objects and other objects of the present invention as hereinafter will become more readily apparent can be attained by molded bodies which are comprised of strongly acidic, weakly acidic, or basic macroporous ion exchange resins, or gel-like resins in the form of separative bodies, which have an internal voids fraction (pore voids fraction in relation to the same macro form but without pores) of 5-95 vol %, a BET surface of 0.01-1,000 sq m/g, and an ion exchange capacity of 0.05-10 meq/g.

BRIEF DESCRIPTION OF THE DRAWINGS

A more complete understanding of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

The shaped or molded bodies of the present invention may be used as packings in chemical engineering to increase reaction rates by increasing the surface between gaseous materials or even between liquids in countercurrent or concurrent flow, which packings may be, in the form of Raschig rings, berl saddles, torus saddles, packing rings with crossbars (Lessing rings) or dual intersecting crossbars, pall rings, or other hollow bodies, hollow balls, or the like.

The molded bodies preferably have a BET surface area of 20-60 sq m/g and an ion exchange capacity of preferably 3-6 meq/g. The BET surface area is measured according to the Haul-Duembgen single point difference method (DIN 66 132).

The molded bodies are advantageously produced by polymerization which is initiated by addition of a radical-providing initiator, in the copolymerization of styrene and divinylbenzene in a ratio of 200:1 to 1:8 by weight, preferably 20:1 to 5:1, possibly with addition of poreformers in the amount of 2-80 wt. %, preferably 10-40 wt. % based on the entire mixture.

An important group of molded bodies is produced from strongly acid macroporous ion exchange resins by generating or providing acid centers, particularly by subsequent treatment with acid, e.g. a sulfonic acid.

For certain reactions it is advantageous to dope molded bodies of the above-described type with metals of Group VIIA or VIIIA of the Periodic Table, particularly Pd, Pt, Ru, or Rh, in amounts of 0.1-100 g/liter of ion exchange resin.

An advantageous exterior shape of the above-described molded bodies is that of Raschig rings having an interior diameter of 0.5-100 mm, preferably 4-20 mm, a wall thickness of 0.1-20 mm, preferably 0.5-3 mm, and a length 0.1-20 times the interior diameter.

An aspect of the invention is in the use of the above-described molded bodies as catalytically active packing bodies for chemical reactions or combinations of chemical reactions, particularly etheration, hydration, dimerization, oligomerization, esterification, hydrogenation, and alkylation. A particularly preferred use of the molded bodies is in a process in which chemical reaction(s) and separation occur simultaneously, with the separation being, e.g., adsorption, absorption, extraction, stripping, distillation, rectification, fractionation, membrane separation, or the like.

The manufacture and use of an ion exchange resin as a molded body enables the ion exchanger to be employed simultaneously as a packing body to create an interphase surface and to serve as a catalyst in a packed reaction column. The manufacture of the novel packing bodies, having dimensions, e.g., of a customary 7 mm Raschig rings with wall thicknesses of 1 mm, enables one for the first time to have a bed of ion exchange material which has sufficient voids fraction to conduct countercurrent gas-liquid unit operations.

Further, the uniform material strength enabled by the present molded bodies is advantageous for rational reaction systems. Such uniform strength was not achieved in previous attempts to convert individual small spheres of ion exchange resin into larger bodies with an appropriate voids fraction by combining a plurality of individual spheres.

Suitable ion exchange resins which can be employed particularly include resins comprised of divinylbenzene-styrene copolymers (DVB-styrene copolymers), and also phenol-formaldehyde resins, urea resins, and condensation products of aromatic diamines with formaldehyde.

The molded bodies may be produced by block polymerization of the monomer mixture in appropriate gravity molds, e.g. by ring gap polymerization in polytetrafluoroethylene (poly-TFE) gravity molds. Other apparatuses are also suitable, e.g. extruders or injection molding machines, as well as other apparatuses for forming polymerization mixtures in the process of hardening, which other apparatuses are known to those skilled in the art.

Gel-like resins are also suitable for forming the molded bodies. The resins can be processed in suitable apparatuses to form the desired packing bodies. Thus, it is also possible to perform forming operations on incompletely hardened resins which are still formable, to produce said packing bodies, wherewith suitable conditions are imposed after the forming to bring about final hardening to obtain the required strength properties for use of the bodies as packing in process engineering equipment.

The addition of an inert pore-former such as alkanes, e.g. n-pentadecane, in a specified relative amount, enables the desired macroporous structure to be achieved according to specifications. Other adjuvants which may be used are polymerization initiators such as, e.g. azoisabutyronitrile (AIBN).

In strongly acid macroporous ion exchange resins comprised of polystyrene crosslinked with divinylbenzene, the charge carriers in the form of $SO_3H$ groups anchored on the polymer matrix by sulfonation are responsible for both the ion exchange capacity and the catalytic activity of the resins.

The specified interior surface area values are achieved by means of the macroporous structure, which structure corresponds to that of common macroporous materials which are commercially available.

The manufacture of Raschig rings comprised of a special macroporous, strongly acid resin comprised of DVB-styrene copolymer will be described hereinbelow.

EXAMPLE 1

A monomer mixture comprised of styrene and divinylbenzene in a weight ratio of 13:1 was produced. n-Pentadecane was added in the amount of 35 wt. %, as a poreformer, and an effective amount of AIBN was added, as a polymerization initiator. The mixture was then ready to be charged into a gravity mold.

The gravity mold was in the form of poly-TFE tubing which is interiorly and exteriorly reinforced and which creates a ring-shaped cavity. Two poly-TFE ring segments served for sealing and as spacers. The ring-shaped cavity had an interior diameter of 4 mm and a wall thickness of 0.5 mm.

The mixture was allowed to react 5 hr at 80° C., following which the cast piece was removed from the mold and cut to length by sawing. To remove the n-pentadecane from the molded bodies, a first washing with chloroform was carried out.

For sulfonation, 350 ml of the Raschig rings manufactured as above were allowed to react with 600 ml chloroform and 80 ml chlorosulfonic acid in a round-bottomed flask in an ice bath, under reflux cooling and with occasional stirring, for 20 hr. Then an additional 40 ml chlorosulfonic acid was added, and the mixture was allowed to react another 3-5 hr at room temperature.

The sulfonated rings were then washed with chloroform, followed by methanol, and then water, until a pH of at least 3.0 was reached. The rings were stored in distilled water.

The strongly acidic molded bodies comprised of macroporous strongly acidic resins may be coated with one or more metals of group VIIA or VIIIA of the Periodic Table in the following manner: First, the molded bodies are treated with a solution of the desired metals, e.g. an aqueous solution of non-complexed cationic salts. Such metal salts may be, e.g. chlorides, bromides, nitrates, sulfates, and/or acetates. The amount of the salts is chosen such that the desired amount of metal is present on the molded bodies after further treatment, which further treatment may be, e.g., in particular, reduction. After the treatment with metal salt solution, the molded bodies are washed to neutrality with water and are dried, e.g. at elevated temperature and possibly at reduced pressure. The deposited metals are converted to the elemental state by treatment with a reducing agent such as hydrogen, e.g. at a pressure of 2-50 bar, preferably 20-50 bar, and at a temperature of 50°-140° C., preferably 80°-120° C.

The molded bodies are suitable for use as catalytically active packing bodies for single phase and multiphase gas and liquid reactions, particularly with countercurrent flow of the phases, in that the bodies have a high voids fraction and therefore impose a low pressure drop.

The molded bodies are particularly well suited for use as catalytically active packing bodies for so-called catalytic distillations, wherein the reaction and the subsequent processing of the reaction products, which processing is ordinarily carried out in a further process step, are carried out simultaneously in a reaction apparatus with distillation or rectification.

The molded bodies are advantageously installed in the reactor as loose beds on grates. The inlet and outlet of the reactor may be provided with coarse filter fabric to retain small particles, fragments, particles due to wear, or the like, and to prevent them from being entrained in the flow. To reduce mechanical stress, the molded bodies can be disposed an a plurality of grates mounted one above the other. Particularly suitable chemical reactions for this type of operation are reactions wherein the boiling points of the reactants and products are different.

Figure 1:
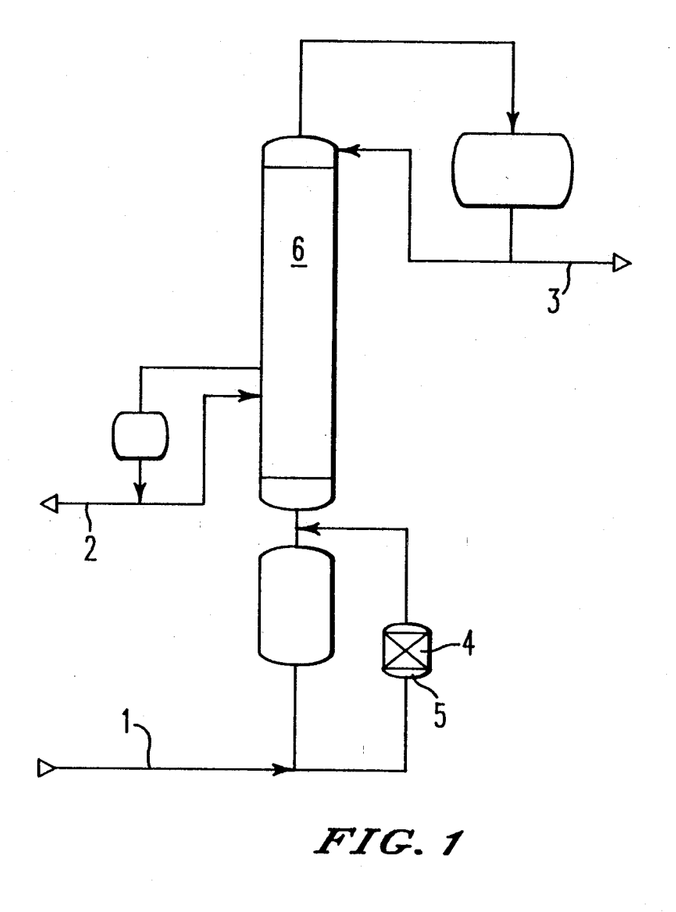
FIGS. 1 to 3 illustrate apparatus embodiments in which the molded bodies of the invention can be used to effect separation of reactants and products by boiling point differences.
Figure 2:
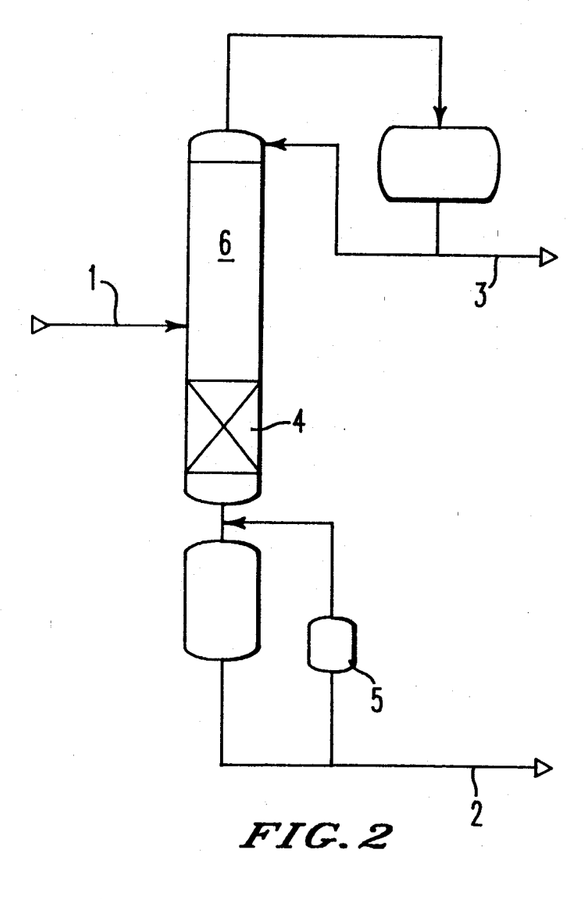
Figure 3:
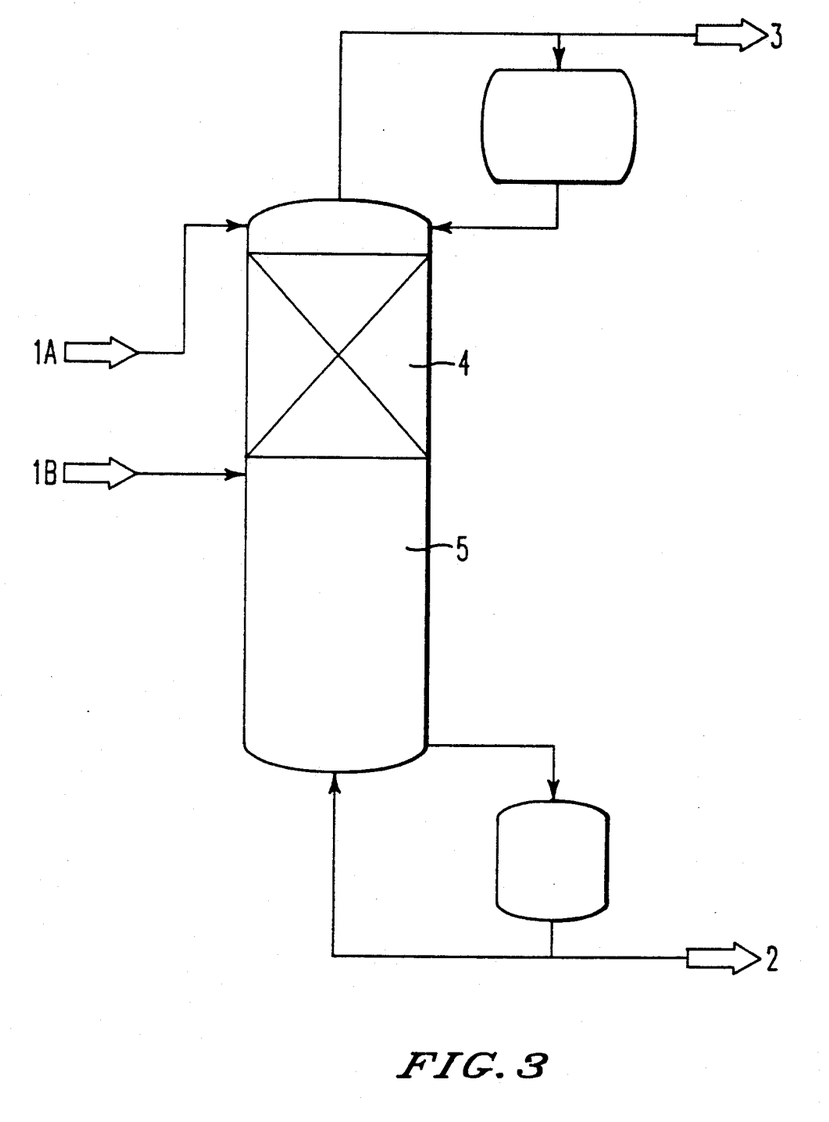

Examples of applications are the following, according to exemplary embodiments as illustrated schematically in FIGS. 1-3:

1. The reaction products have lower boiling points than the initial mixture.

The initial mixture passes via line 1 into the reboiler 5 which is filled with molded bodies 4. The reaction products produced are separated according to their boiling points in the rectifier column 6, and are removed through lines 2 and 3 (FIG. 1).

2. The boiling points of some of the products are higher than that of the initial mixture, and those of other products are lower than that of the initial mixture.

The initial mixture is introduced through line 1 above the bed of molded bodies 4. In the bed it is converted into a low-boiling and a higher-boiling component. At the top of the rectification column 6 the low-boiling component is withdrawn through line 3, and at the sump the higher-boiling component is withdrawn through line 2 (FIG. 2).

3. The example illustrated in FIG. 3 concerns the case in which the stream of the initial mixture 1B is comprised of a plurality of components which do not differ significantly in their boiling points, but considered overall the boiling point of the mixture is a minimum. The stream of initial mixture 1A is comprised of only a single component and has a boiling point slightly above that of reaction product 2 but substantially above that of initial mixture stream 1B and that of overhead product 3.

The higher-boiling initial mixture stream 1A is fed at the head of the rectifier column 5, above the catalyst ring packing 4. The lower-boiling stream is fed in the middle, below the said packing, in column 5. In accordance with their boiling points, the components of stream 1A tend to concentrate in the bottom half of the column, and the components of stream 1B tend to concentrate at the head of the column. In the process, however, the components of 1A react with a component 1B highly selectively, to form high-boiling product stream 2 which can be drawn off in the sump. The distillate 3, reduced by one component, can be sent to further processing (FIG. 3).

The "catalytic distillation" has the advantage of eliminating one process step, thereby reducing apparatus cost, and also has process advantages. The process, which is particularly preferred for exothermic reactions, enables direct utilization of the liberated heat of reaction namely in the simultaneous distillation of the reaction products. The reaction temperature is set so as to correspond to the boiling point of the product, whereby temperature is readily controlled.

The reaction product formed is removed immediately, by simultaneous distillation in the reaction zone, thereby minimizing sequential and parallel byproducts. The rapid withdrawal of the reaction product enables equilibrium reactions to be carried out essentially to completion. New reaction product is formed at once, in accordance with the equilibrium constant.

Reactions which can be carried out according to this principle of catalytic distillation ar exothermic reactions such as etherification, e.g. production of MTBE from methanol and isobutene; hydration, e.g. production of isopropanol from propene and water; dimerization, e.g. of isobutene to form diisobutene; esterification, e.g. of acetic acid with isopropanol to form isopropyl acetate; alkylation, e.g. of phenol with propene to form propylphenol; and oligomerization, e.g. of butenes to form valuable components of so-called alkylated gasoline.

The molded bodies are suited as bifunctional catalytically active packing bodies for catalytic reactions of hydration and etherification with simultaneous hydrogenation. An example is etherification of pyrolytic light gasoline to tert-amyl methyl ether with simultaneous selective hydrogenation of dienes, e.g. cyclopentadiene and its derivatives, to the corresponding monoolefins.

Also, the decomposition of MTBE into isobutene and methanol can be carried out according to the catalytic distillation process principle. This provides a technique of obtaining highly purified products (in the present case, highly purified isobutene). Another possible use is separation of isoamylene from a $C_5$ cut, wherewith first a tertiary amyl alkyl ether is formed by catalytic distillation, and this is decomposed in a second catalytic distillation to form highly purified isoamylene and the alcohol.

The inventive molded bodies used as a packing material for catalytic distillations have critical advantages over ordinary commercially available ion exchange materials comprised of DVB-styrene copolymer and supplied as small spheres. They function simultaneously as packing bodies to create a phase boundary and as catalysts. This dual function is made possible by the low pressure drop of the molded bodies.

Reaction studies have shown that the present molded bodies have the same activity as comparable customary catalysts. There is the additional advantage of having available a catalytically active ion exchange resin in the form of molded bodies, wherewith the high voids fraction of the molded bodies enables them to be used as packing bodies where they provide optimum heat- and mass transfer between the operative fluid phases.

The following comparative test results for the example of MTBE synthesis indicate that the molded bodies comprised of ion exchange resin have comparable catalytic activity (Example 2) to an ordinary commercially available catalyst (viz. Amberlyst ® 15) supplied in the form of particles with mean diameter 0.2-2 mm (Comparison Example 3).

EXAMPLE 2

Figure 4:
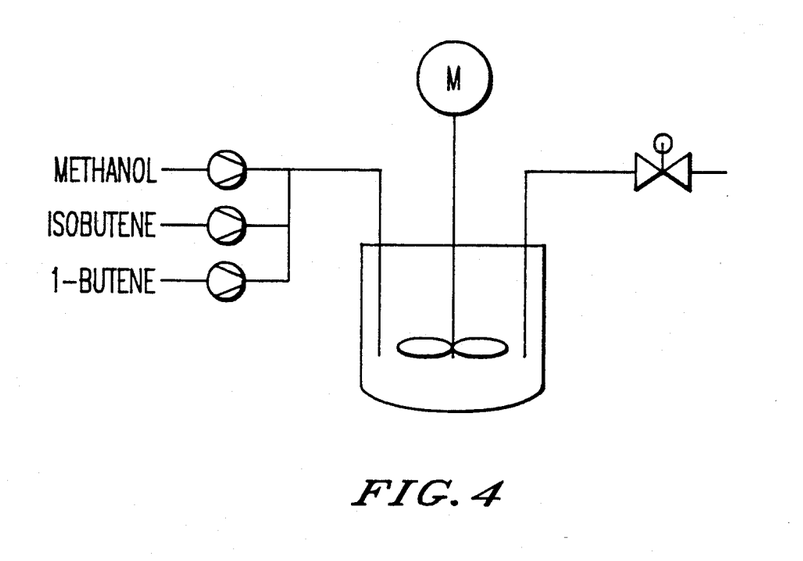
FIG. 4 shows a heated reaction vessel containing molded bodies of the invention as they ar used in MTBE synthesis.

To study the reaction kinetics of MTBE synthesis, the reactants methanol and isobutene, along with the diluent medium 1-butene, were fed with metering pumps into a cylindrical heated reaction vessel of a 106 ml capacity as shown in the schematic of FIG. 4. The volumetric flow was chosen such that the mean residence time in the reactor was 5.3 min. In the reactor, the catalyst rings were borne on a fixed poly-TFE tube. Samples were taken via a partial stream of the outlet mixture, which was passed continuously through a sample withdrawal loop. The results obtained for the parameters employed are presented in the following Table 1.

| Reaction equations: | MEOH + IB → MTBE |
|---|---|
| | IB + IB → DIB. |
| Reaction conditions: | T = 60° C., p = 21 bar. |

Catalyst bed: 1.0 g Raschig rings comprised of strongly acidic macroporous DVB-styrene copolymer, with dimensions (after swelling in water) of 6×6×1 mm. Swelling (based on the dried state) 80 vol %. Voids fraction c. 45 vol %. Degree of crosslinking: 7.5 wt. % divinylbenzene in the monomer mixture with styrene. BET surface area (1-point method, $N_2$ adsorption) 30 sq m/g. Ion exchange capacity 4.5 meq/g.

The initial reaction rate determined is practically as high for the catalyst rings according to the invention as for Amberlyst ® 15 employed under comparable conditions, as seen by comparison with Example 3, infra.

TABLE 1

| | Concentrations (wt %) | | | | | Conversion | Reaction Rates in mmol/sec/eq. | |
|---|---|---|---|---|---|---|---|---|
| No. | MeOH | IB | 1B | MTBE | DIB | (MeOH) in % | DIB | MTBE[1] |
| 1 | 42.7 | 55.7 | — | 1.63 | — | 1.37 | — | 16.8 |
| 2 | 30.8 | 57.8 | 9.43 | 1.97 | — | 2.27 | — | 19.5 |
| 3 | 16.9 | 60.5 | 20.0 | 2.51 | 0.088 | 5.12 | 0.66 | 23.9 |
| 4 | 5.96 | 62.5 | 29.6 | 1.40 | 0.507 | 7.86 | 8.45 | 29.7 |
| 5 | 4.53 | 63.1 | 30.4 | 1.41 | 0.556 | 10.2 | 9.24 | 29.8 |
| 6 | 3.03 | 63.2 | 31.5 | 1.53 | 0.740 | 15.5 | 12.2 | 32.3 |

1: MeOH = methanol
2: IB = Isobutene
3: 1B = 1-butene
4: MTBE = methyl-tert-butylether
5: DIB = diisobutene (1,2,4-trimethyl-1-pentene and 2,2,4-trimethyl-2-pentene)

EXAMPLE 3 (COMPARISON EXAMPLE)

The following test results were obtained under the same conditions as in Example 2, with the sole difference being that the catalyst here was in the form of spheres and was no longer fixed in the reactor but was maintained in suspension by the stirrer. The weight of the catalyst used was also 1.0 g.

| | Concentration in wt % | | | | | Conversion | Reaction Rates in mmol/sec/eq. | |
|---|---|---|---|---|---|---|---|---|
| No. | MeOH | IB | 1B | MTBE | DIB | (MeOH) in % | DIB | MTBE |
| 1 | 39.2 | 55.0 | 5.22 | 0.544 | — | 0.502 | — | 18.2 |
| 2 | 22.0 | 58.0 | 19.4 | 0.549 | — | 0.898 | — | 17.5 |
| 3 | 9.2 | 61.0 | 28.7 | 1.02 | 0.097 | 3.870 | 2.30 | 31.3 |
| 4 | 4.25 | 60.3 | 33.2 | 1.88 | 0.295 | 13.800 | 6.18 | 56.8 |
| 5 | 2.72 | 60.2 | 34.3 | 2.34 | 0.474 | 23.800 | 9.21 | 70.6 |

1: MeOH = methanol
2: IB = Isobutene
3: 1B = 1-butene
4: MTBE = methyl-tert-butylether
5: DIB = diisobutene (2,2,4-trimethyl-1-pentene and 2,2,4-trimethyl-2-pentene)

EXAMPLE 4

Figure 5:
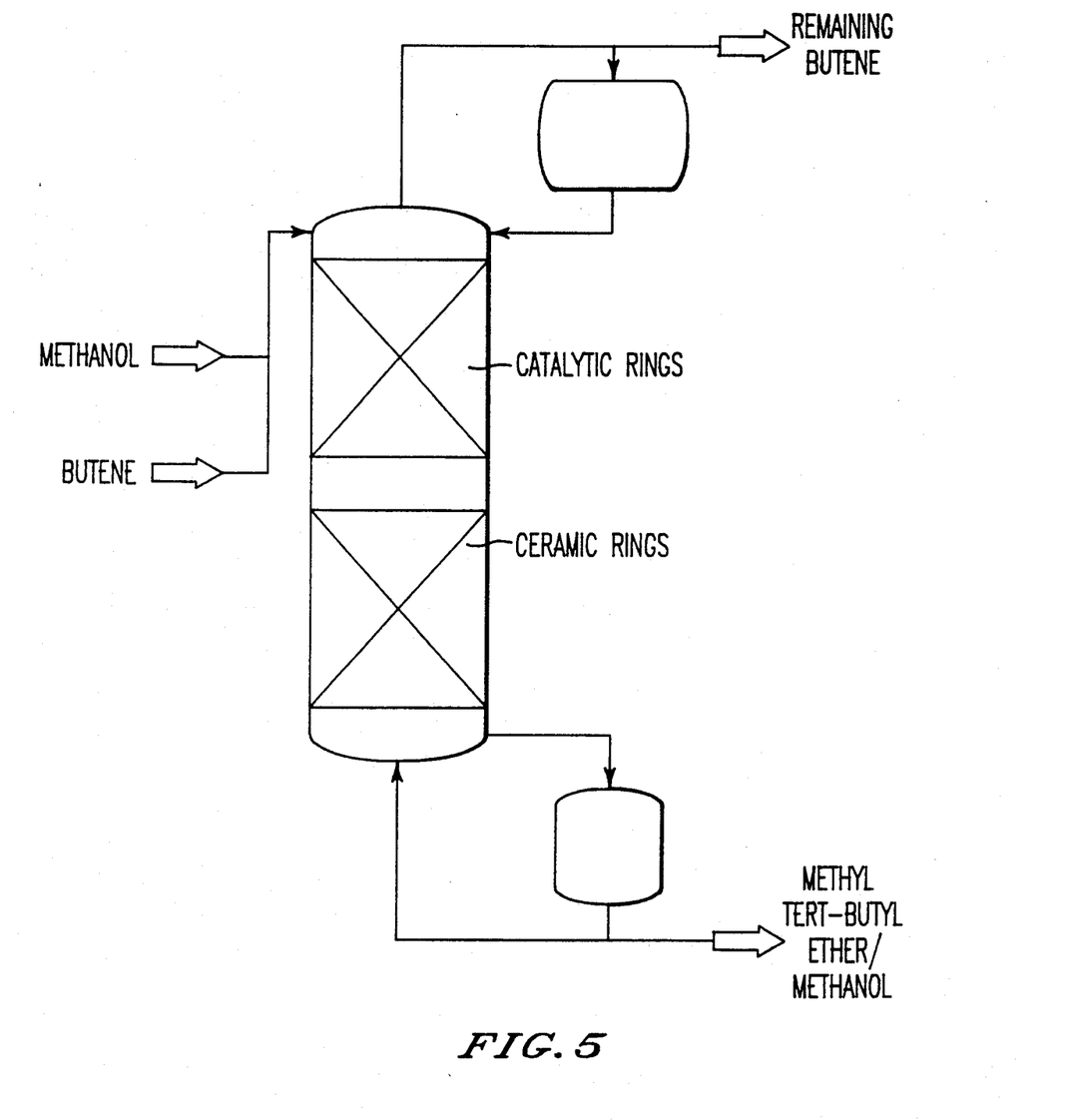
FIG. 5 shows an apparatus scheme which has a packing column on a component which contains molded bodies in the form of Raschig rings, as the apparatus is used in MTBE synthesis.

In further tests, the inventive catalyst rings were employed in a packing column comprised of stainless steel material (tool steel no. 1.4571). The reacting methanol and isobutene, along with the diluting medium 1-butene, were fed to the head of the column by metering pumps. The mixture was heated to approximately boiling temperature. The upper half of the separating column was filled with the chemically active molded bodies in the form of catalytic Raschig rings, and the bottom half was filled with inert ceramic rings of the same dimensions (see FIG. 5). The interior diameter of the column was 53 mm. The total height of the beds of packing bodies was 1 m. To reduce mechanical stress, the catalytic rings were supported on three grates disposed one above the other.

Samples were taken via partial streams of the overhead and bottoms products, which streams were passed continuously through sampling tubes.

In the following Tables, the results of Test Runs 1 to 9 are given, which runs were carried out in the above described apparatus. The feed stream was at a rate of 25 ml/min. Apparatus pressure was 6 bar abs. The temperature below the catalyst bed was 80° C. The molar compositions of the feed (%) for the various runs were:

| Nr. | $X_{MeOH}$ | $X_{1B}$ | $X_{IB}$ |
|---|---|---|---|
| 1 | 25.0 | 63.75 | 11.25 |
| 2 | 25.0 | 50.5 | 24.5 |
| 3 | 25.0 | 37.5 | 37.5 |
| 4 | 52.5 | 23.5 | 24.0 |
| 5 | 52.5 | 32.0 | 15.5 |
| 6 | 52.5 | 40.5 | 7.0 |
| 7 | 80.0 | 10.0 | 10.0 |
| 8 | 80.0 | 13.5 | 6.5 |
| 9 | 80.0 | 17.0 | 3.0 |

The molar compositions of the bottoms products were as follows:

α-Di = α-diisobutylene = 2,4,4-trimethyl-1-pentene.
β-Di = β-diisobutylene = 2,4,4-trimethyl-2-pentene.
α-Tri = α-triisobutylene = 2,4,4,6,6-pentamethyl-1-heptane.
β-Tri = β-triisobutylene = 2,4,4,6,6-pentamethyl-2-heptene.

| No. | $X_{MIBF}$ | $X_{MeOH}$ | $X_{\alpha DI}$ | $X_{\beta DI}$ | $X_{Tri}$ | $X_{\beta Tri}$ | IB Conversion |
|---|---|---|---|---|---|---|---|
| 1 | 73.08 | 26.92 | traces | 0 | 0 | 0 | 58.79 |
| 2 | 84.01 | 15.99 | traces | traces | 0 | 0 | 70.07 |
| 3 | 67.78 | 14.48 | 12.83 | 4.305 | 0.28 | 0.326 | 79.02 |
| 4 | 44.75 | 55.25 | traces | traces | traces | traces | 71.65 |
| 5 | 22.94 | 76.89 | 0.085 | 0.083 | traces | traces | 69.40 |
| 6 | 9.29 | 90.71 | 0 | 0 | 0 | 0 | 66.06 |

-continued

α-Di = α-diisobutylene = 2,4,4-trimethyl-1-pentene.
β-Di = β-diisobutylene = 2,4,4-trimethyl-2-pentene.
α-Tri = α-triisobutylene = 2,4,4,6,6-pentamethyl-1-heptane.
β-Tri = β-triisobutylene = 2,4,4,6,6-pentamethyl-2-heptene.

| No. | $X_{MIBF}$ | $X_{MeOH}$ | $X_{\alpha DI}$ | $X_{\beta DI}$ | $X_{Tri}$ | $X_{\beta Tri}$ | IB Conversion |
|---|---|---|---|---|---|---|---|
| 7 | 13.52 | 86.48 | 0 | 0 | 0 | 0 | 84.98 |
| 8 | 6.32 | 93.68 | 0 | 0 | 0 | 0 | 80.12 |
| 9 | 3.44 | 96.56 | 0 | 0 | 0 | 0 | 73.69 |

In connection with the underlying problem of the invention, it may be seen that the bottoms product is free of low-boiling butenes.

In addition to the comparative kinetic studies in packed columns (results given supra), long-term tests were carried out on the service life characteristics of the inventive catalyst, in a tubular reactor with changing catalyst loading.

The reactor employed was a V2A tube of length 770 mm and diameter 20 mm, filled ⅔ with the present catalyst in the form of Raschig rings. The $C_4$ mixture employed was an ordinary commercially available $C_4$ refinery cut containing 10 or 49 wt. % of isobutene. The results of the etherification of isopropanol and methanol, respectively, with isobutene, for selected operating parameters, are summarized in Tables 1 and 2.

By inserting a water wash and a so-called "police filter" ahead of the entry of the $C_4$ cut into the reaction/separation column, one can effectively remove impurities which may reduce the activity of the catalyst, e.g. weak bases such as amines or cations such as sodium. Depending on the quality of the methanol feed stream, a police filter may also be commended. The rate of mechanical defects in the catalyst rings has proved to be low. Catalyst rings comprised of sulfonated macroporous styrene polymer were used which had a diameter of about 6 mm and length of 8 mm. The color of the hollow cylinders was white to cream. The ion exchange capacity was 4.44 mg $H^+$ per g dry catalyst as determined by the method of Fisher and Kunin, 1955 *Analyt. Chem.*, 27, 1191–1194). The swollen volume of 23 ml dry catalyst in wet form (by water or methanol) was 50 ml, corresponding to a bed density of 0.275 g/ml dry and 0.127 g/ml wet. The degree of crosslinking of the catalyst used corresponds to the nominal percentage of divinylbenzene in the initial monomer mixture. The BET surface area of the catalyst was determined by the 1-point method, with $N_2$ adsorption.

The inventive molded bodies in the form of hollow cylinders comprised of sulfonated styrene polymer were tested with the following reactions, with good success, in addition to the above-reported test runs an etherification of isobutene cuts with isopropanol and with methanol. The same apparatus was used as with the above-described long term studies.

1. Hydration of propane with water (Table 3).
2. Hydration of isobutene with water (Table 4).
3. Etheration of 2-methyl-2-butene with methanol (Tabel 5).
4. Dimerization of iso-$C_4$ (Table 6).

In addition, the present hollow cylinders comprised of sulfonated macroporous styrene polymer were doped with palladium and tested for suitability for use as catalysts for hydrogenative etherification.

The doping with palladium was carried out as follows: 0.63 $Pd(NO_3)_2 \cdot 2H_2O$ was dissolved in 60 ml water. The solution was a brownish yellow color. 100 ml water-moist styrene polymer molded bodies was added. The styrene polymer was completely covered by the palladium nitrate solution. After standing 1 day, the aqueous solution was water-clear, indicating exchange of the Pd.

The feeds used were ordinary commercial methanol and light gasoline from an olefin unit.

After the molded bodies were installed in the above-described tubular reactor, the residual water present in the Raschig rings was purged with methanol, and the palladium was reduced with 6 liter (STP) hydrogen in 150 ml methanol per hr, at 70° C. and 11 bar. After 48 hr, methanol was replaced by the reaction feed mixture comprising gasoline and methanol.

Catalyst amount: 100 ml (swollen in water).
Temperature: 70°–75° C.
Pressure: 10–11 bar.
Feed: Crack-L distillate from VC, with 10% of methanol.
Feed rate: 150 ml/hr = 103 g/hr.
$H_2$ rate: 7 liter (STP) per hr.
Bi/$H_2$ ratio: 200 g/g.

The test showed that the present molded bodies strongly doped with palladium very selectively hydrogenate the unsaturated olefins (dienes) present in pyrolytic light gasoline, and also catalyze the etheration of tertiary monoolefins with primary and secondary alcohols. The results are shown in Table 7.

TABLE 3

| | Etherification of $C_4$ Cut With Isopropanol | | | | | | | | |
|---|---|---|---|---|---|---|---|---|---|
| | Test Number | | | | | | | | |
| | 1 | 2 | 3 | 4 | 5 | 6 | 7 | 8 | 9 |
| Catalyst Volume (swollen) (ml) | 160 | 160 | 160 | 160 | 160 | 160 | 160 | 160 | 160 |
| LHSV (ml feed/ml catalyst) | 2.46 | 2.46 | 2.46 | 2.46 | 2.46 | 2.46 | 2.46 | 2.46 | 4.92 |
| Molar ratio (Isobutene:Isopropanol) | 0.5 | 0.5 | 0.5 | 0.5 | 0.5 | 0.5 | 0.5 | 0.5 | 0.5 |
| Feed Rate | | | | | | | | | |
| $C_4$-Cut (ml/h) | 333 | 333 | 333 | 333 | 333 | 333 | 333 | 333 | 667 |
| Isopropanol (ml/h) | 60 | 60 | 60 | 60 | 60 | 120 | 60 | 60 | 120 |
| Temperature | | | | | | | | | |
| Inlet (°C.) | 53.2 | 53.8 | 54.2 | 58.6 | 58.6 | 58.7 | 58.6 | 58.7 | 58.7 |
| Outlet (°C.) | 55.2 | 56.4 | 57.2 | 59.0 | 59.2 | 59.2 | 59.2 | 59.4 | 59.5 |
| Pressure (bar) | 11 | 11 | 11 | 11 | 11 | 11 | 11 | 11 | 11 |
| Yield Isopropyl-tert. butylether (mol %) | 56.0 | 56.5 | 56.4 | 55.6 | 54.5 | 51.8 | 54.4 | 54.8 | 46.3 |
| Elapsed Time at End of Test (h) | 5 | 12 | 30 | 44 | 65 | 79 | 91 | 105 | 119 |

TABLE 4

Etherification of Isobutene with Methanol

| | Test Number | | | | | | |
|---|---|---|---|---|---|---|---|
| | 1 | 2 | 3 | 4 | 5 | 6 | 7 |
| Catalyst-Volume (swollen) (ml) | 200 | 200 | 200 | 200 | 200 | 200 | 200 |
| LHSV (ml feed/ml catalyst) | 3.98 | 3.99 | 4.03 | 3.97 | 6.80 | 6.84 | 6.85 |
| Molar ratio (Isobutene:Methanol) | 0.83 | 0.83 | 0.85 | 0.83 | 0.84 | 0.83 | 0.82 |
| Feed Rate | | | | | | | |
| $C_4$-Cut (g/h) | 370.6 | 371.0 | 375.6 | 369.9 | 633.3 | 636.3 | 635.2 |
| Methanol (g/h) | 124.3 | 124.8 | 125.1 | 123.5 | 209.4 | 214.6 | 216.5 |
| Temperature | | | | | | | |
| Inlet (°C.) | 59.0 | 58.0 | 59.7 | 60.4 | 49.1 | 48.0 | 49.0 |
| Outlet (°C.) | 62.6 | 62.9 | 62.6 | 62.7 | 67.3 | 65.2 | 65.3 |
| Pressure (bar) | 10 | 10 | 10 | 10 | 10 | 10 | 10 |
| Yield MTBE (Mol %) | 80.1 | 82.1 | 83.4 | 83.3 | 64.6 | 60.4 | 62.1 |
| Elapsed Time at End of Test | 7 | 14 | 21 | 28 | 35 | 42 | 49 |

TABLE 5

Hydration of Propene With Water

| | Test Number | | | | | |
|---|---|---|---|---|---|---|
| | 1 | 2 | 3 | 4 | 5 | 6 |
| Catalyst Volume (swollen) (ml) | 200 | 200 | 200 | 200 | 200 | 200 |
| LHSV (ml feed/ml catalyst) | 1 | 1 | 1 | 0.5 | 0.5 | 0.5 |
| Mole Ratio ($H_2O/C_3$) | 10.3 | 9.2 | 9.8 | 10.2 | 10.4 | 10.3 |
| Feed Rate | | | | | | |
| Propene (g/h) | 32.6 | 32.1 | 32.2 | 15.9 | 15.8 | 15.7 |
| Water (g/h) | 142.0 | 128.0 | 134.0 | 69.0 | 70.0 | 68.5 |
| Outflow rate. as stabilized (g/h) | 144.2 | 131.5 | 139.9 | 73.2 | 74.4 | 73.1 |
| Temperature | | | | | | |
| Inlet (°C.) | 120 | 131 | 142 | 139 | 139 | 138 |
| Outlet (°C.) | 118 | 128 | 138 | 137 | 137 | 137 |
| Pressure (bar) | 80 | 80 | 80 | 80 | 80 | 80 |
| Isopropanol Content of Reaction Product (wt. %) | 2.2 | 3.8 | 6.0 | 8.2 | 8.5 | 8.9 |
| Conversion of Propene (%) | 6.8 | 10.9 | 18.3 | 26.4 | 28.0 | 29.0 |
| Elapsed Contact Time at End of Test (h) | 7 | 14 | 21 | 28 | 35 | 42 |

TABLE 6

Hydration of Isobutene With Water

| | Test Number | | | | | |
|---|---|---|---|---|---|---|
| | 7 | 8 | 9 | 10 | 11 | 12 |
| Catalyst Volume. (swollen) (ml) | 200 | 200 | 200 | 200 | 200 | 200 |
| LHSV (ml feed/ml catalyst) | 0.5 | 0.49 | 0.51 | 0.24 | 0.22 | 0.23 |
| Mole Ratio ($H_2O/i-C_4$) | 10.1 | 10.2 | 10.2 | 12.3 | 11.2 | 9.2 |
| Feed Rate | | | | | | |
| i-Butene (g/h) | 20.2 | 19.7 | 20.7 | 8.4 | 8.3 | 9.7 |
| Water (g/h) | 66.2 | 65.2 | 67.6 | 33.3 | 29.8 | 28.6 |
| Outflow rate. as stabilized (g/h) | 67.7 | 66.9 | 69.3 | 34.3 | 31.0 | 30.0 |
| Temperature | | | | | | |
| Inlet (°C.) | 80.2 | 80.2 | 80.1 | 77.8 | 78.7 | 78.9 |
| Outlet (°C.) | 79.7 | 80.2 | 80.4 | 79.5 | 81.3 | 81.3 |
| Pressure (bar) | 80 | 80 | 80 | 80 | 80 | 80 |
| T-Butanol Content of Reaction Product (wt. %) | 3.0 | 3.3 | 3.0 | 4.1 | 5.2 | 6.1 |
| Conversion of i-Butene (%) | 7.6 | 8.5 | 7.6 | 12.7 | 14.7 | 14.3 |
| Elapsed Contact Time at End of Test (h) | 49 | 56 | 63 | 70 | 77 | 84 |

TABLE 7

| | Test Number | | | | | | | |
|---|---|---|---|---|---|---|---|---|
| | 8 | 9 | 10 | 11 | 12 | 13 | 14 | 15 |
| Catalyst Volume, (swollen) (ml) | 200 | 200 | 200 | 200 | 200 | 200 | 200 | 200 |
| LHSV (ml feed/ml catalyst) | 4.0 | 4.0 | 4.0 | 4.1 | 2.0 | 2.0 | 2.0 | 2.0 |
| Mole Ratio (Meth.-But./MeOH) | 0.84 | 0.92 | 0.91 | 0.92 | 0.90 | 0.89 | 0.87 | 0.87 |
| Feed Rate | | | | | | | | |
| 2-Methyl-2-Butene (g/h) | 364.5 | 374.5 | 375.3 | 379.3 | 185.7 | 185.2 | 184.8 | 184.2 |
| Methanol | 198.6 | 185.8 | 187.4 | 187.9 | 94.7 | 95.3 | 96.6 | 95.9 |
| Temperature | | | | | | | | |
| Inlet (°C.) | 59.0 | 58.0 | 58.0 | 58.0 | 61.3 | 61.2 | 60.8 | 61.3 |
| Outlet (°C.) | 62.6 | 61.5 | 61.9 | 61.9 | 59.9 | 59.8 | 59.7 | 59.8 |
| Pressure (bar) | 10 | 10 | 10 | 10 | 10 | 10 | 10 | 10 |

TABLE 7-continued

|  | Test Number | | | | | | | |
|---|---|---|---|---|---|---|---|---|
|  | 8 | 9 | 10 | 11 | 12 | 13 | 14 | 15 |
| Yield TAME* (Mol %) | 26.9 | 24.3 | 25.0 | 23.7 | 37.3 | 37.3 | 37.4 | 37.5 |
| Elapsed Contact Time at End of Test (h) | 140 | 147 | 154 | 161 | 168 | 175 | 182 | 189 |

*TAME = T-Amyl Methyl ether

TABLE 8

Dimerization of Isobutene

|  | Test Number | | | | | | |
|---|---|---|---|---|---|---|---|
|  | 1 | 2 | 3 | 4 | 5 | 6 | 7 |
| Catalyst Volume (swollen) (ml) | 200 | 200 | 200 | 200 | 200 | 200 | 200 |
| LHSV (ml feed/ml catalyst) | 1 | 1 | 1 | 1 | 1 | 1 | 2 |
| Feed Rate | | | | | | | |
| C$_4$-Mixture (g/h) | 118.5 | 117.7 | 114.3 | 113.7 | 116.7 | 116.7 | 233.0 |
| i-Butene*) (g/h) | 57.8 | 57.4 | 55.8 | 55.9 | 56.9 | 54.8 | 109.5 |
| Temperature | | | | | | | |
| Inlet temperature (°C.) | 73.8 | 74.4 | 72.2 | 72.5 | 82.8 | 82.6 | 90.1 |
| Pressure (bar) | 20.0 | 20.0 | 20.0 | 20.0 | 20.0 | 20.0 | 20.0 |
| Yield of Dimer (Mol %) | 92.9 | 94.4 | 95.8 | 93.5 | 93.5 | 94.3 | 96.3 |
| Catalyst-Elapsed Time (h) | 197 | 205 | 213 | 221 | 245 | 253 | 261 |

*) Present in C$_4$-Mixture

TABLE 9

Etherification Under Hydrogenation Conditions

| Component |  | Feed | Reaction Product |
|---|---|---|---|
| Methanol | (wt. %) | 10.5 | 6.8 |
| Sum of 2-Methylbutenes | (wt. %) | 17.4 | 12.8 |
| Sum of 2-Methylpentenes | (wt. %) | 5.7 | 4.6 |
| Cyclopentadiene | (wt. %) | 0.59 | <0.005 |
| cis-Pentadiene-1,3 | (wt. %) | 0.12 | <0.005 |
| trans-Pentadiene-1,3 | (wt. %) | 0.21 | <0.005 |
| Methylbutadiene | (wt. %) | 0.11 | <0.005 |
| TAME | (wt. %) | — | 6.7 |
| 2-Methoxy-2-methylpentane | (wt. %) | — | 1.5 |
| Other Oxygen Containing Components | (wt. %) | — | 2.1 |

What is claimed as new and desired to be secured by Letters Patent of the United States is:

1. Molded bodies in the form of packing bodies consisting of a macroporous strongly acid or basic ion exchange resin having a voids fraction of 5-95 vol % of the macro shape without pores, a BET surface area of 0.1-1,000 sq m/g, and an ion exchange capacity of 0.05-10 meq/g, which are formed of a macroporous strongly acid or basic ion exchange resin prepared by copolymerizing monomers consisting of styrene and divinylbenzene in a weight ratio of 200:1 to 1:8, in the presence of a polymerization initiator.

2. The molded bodies according to claim 1, which are formed of a macroporous strongly acid ion exchange resin prepared by generating or introducing acid centers therein by subsequent acid treatment.

3. The molded bodies according to claim 1, which are doped with at least one metal of group VIIA or VIIIA of the Periodic Table in amounts of 0.1-100 g/liter of ion exchange resin.

4. The molded bodies according to claim 1, in the form of Raschig rings having an interior diameter of 0.5-100 mm, a wall thickness 0.1-20 mm, and a length 0.1-20 times the interior diameter.

5. The molded bodies according to claim 1, wherein the molded bodies are in the form of Raschig rings, berl saddles, torus addles, packing rings with crossbars, dual intersecting crossbars, pall rings or hollow bodies.

6. The molded bodies according to claim 1, wherein said BET surface area ranges from 20-60 sq m/g and said ion exchange capacity ranges from 3-6 meq/g.

7. The molded bodies according to claim 1, wherein said weight ratio of monomers ranges from 20:1 to 5:1 and said copolymerizing is carried out in the presence of a pore former in an amount of from 10-40 wt. % in the entire mixture.

8. The molded bodies according to claim 3, wherein said metal is Pd, Pt, Ru or Rh.

9. The molded bodies according to claim 4, wherein said interior diameter ranges from 4-20 mm and said thickness ranges from 0.5 to 3 mm.

10. The molded bodies according to claim 1, consisting of said macroporous strongly acid or basic ion exchange resin formed of monomer consisting of said styrene and divinylbenzene.

* * * * *